(12) United States Patent
Suwa et al.

(10) Patent No.: US 8,744,044 B2
(45) Date of Patent: Jun. 3, 2014

(54) X-RAY IMAGING APPARATUS

(75) Inventors: Hidetomo Suwa, Machida (JP);
Masaaki Kobayashi, Shimotsuke (JP);
Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 302 days.

(21) Appl. No.: 13/262,029

(22) PCT Filed: Apr. 22, 2010

(86) PCT No.: PCT/JP2010/057646
§ 371 (c)(1),
(2), (4) Date: Sep. 29, 2011

(87) PCT Pub. No.: WO2010/143481
PCT Pub. Date: Dec. 16, 2010

(65) Prior Publication Data
US 2012/0039441 A1  Feb. 16, 2012

(30) Foreign Application Priority Data
Jun. 8, 2009  (JP) .................................. 2009-137724

(51) Int. Cl.
*G01N 23/04* (2006.01)
*H05G 1/64* (2006.01)

(52) U.S. Cl.
USPC .......................................... 378/62; 378/98.8

(58) Field of Classification Search
USPC .................... 378/62, 98.8, 167, 189
See application file for complete search history.

(56) References Cited

U.S. PATENT DOCUMENTS

| | | | | |
|---|---|---|---|---|
| 6,030,119 | A  * | 2/2000 | Tachibana et al. | 378/169 |
| 6,592,257 | B1 * | 7/2003 | Heidsieck et al. | 378/189 |
| 7,104,686 | B2 | 9/2006 | Watanabe et al. | 378/189 |
| 7,210,847 | B2 * | 5/2007 | Hack | 378/189 |
| 7,734,016 | B2 | 6/2010 | Watanabe | 378/145 |
| 7,889,843 | B2 | 2/2011 | Watanabe | 378/116 |
| 7,924,982 | B2 | 4/2011 | Watanabe | 378/114 |
| 2010/0254517 | A1 | 10/2010 | Watanabe | 378/154 |
| 2011/0049371 | A1 | 3/2011 | Kobayashi | 250/361 R |
| 2011/0163240 | A1 | 7/2011 | Suwa et al. | 250/370.09 |

FOREIGN PATENT DOCUMENTS

| | | |
|---|---|---|
| JP | 2006-212175 | 8/2006 |
| JP | 2006-343787 | 12/2006 |
| JP | 2008-051281 | 3/2008 |
| JP | 2008-311298 | 12/2008 |
| JP | 2009-042350 | 2/2009 |
| JP | 2009-230000 | 10/2009 |

* cited by examiner

*Primary Examiner* — Irakli Kiknadze
(74) *Attorney, Agent, or Firm* — Fitzpatrick, Cella, Harper & Scinto (57) ABSTRACT

An X-ray imaging apparatus includes an X-ray irradiation unit which irradiates X-rays, a detection unit which detects the X-rays transmitted through an object, and a housing which contains the detection unit. The housing includes a first housing in which an X-ray transmission member which transmits the X-rays is placed in an incident range of the X-rays irradiated from the X-ray irradiation unit; a second housing which supports the detection unit while being spaced apart from the X-ray transmission member on an opposite side to an incident side on which the X-rays strike the X-ray transmission member; and a plurality of connecting members which connect the first housing to the second housing.

7 Claims, 9 Drawing Sheets

X-RAY IMAGING APPARATUS

TECHNICAL FIELD

The present invention relates to an X-ray imaging apparatus.

BACKGROUND ART

Conventionally, apparatuses which obtain radiographic images of objects by irradiating the objects with X-rays and detecting the intensity distributions of X-rays transmitted through the objects have been widely and generally used in the fields of industrial nondestructive testing and medical diagnosis. As a general method for such imaging, a film/screen method using X-rays is available. This method images by using a combination of a photosensitive film and a phosphor having sensitivity to X-rays. Rare-earth phosphor sheets which emit light upon application of X-rays are held in tight contact with the two surfaces of a photosensitive film. The phosphor converts X-rays transmitted through an object into visible light. The photosensitive film then captures the light. The method then develops, by chemical treatment, the latent image formed on the film, thereby visualizing the image.

The recent advances in digital technology have popularized the scheme of obtaining high-quality radiographic images by converting the intensity distribution of X-rays transmitted through an object into an electrical signal, detecting it, processing it, and then reproducing the resultant information as a visible image on a monitor or the like. As such a method of converting a radiographic image into an electrical signal, there has been proposed a radiographic image recording/reproduction system which temporarily stores X-rays transmitted through an object as a latent image in a phosphor, photoelectrically reads out the latent image by irradiating the phosphor with excitation light such as a laser beam, and then outputs the readout image as a visible image.

In addition, with the recent advances in semiconductor process technology, there has been developed an apparatus for capturing a radiographic image in the same manner as described above by using a semiconductor sensor. These systems have very wide dynamic ranges as compared with conventional radiographic systems using photosensitive films, and can obtain radiographic images which are robust against the influences of variations in the X-ray dose upon exposure. At the same time, unlike the conventional photosensitive film scheme, this method need not perform any chemical treatment and can instantly obtain an output image.

Recently, a portable imaging apparatus like that disclosed in Japanese Patent Laid-Open No. 2006-212175 has been proposed. This reference discloses a structure configured to engage pins provided on the housing side in holes provided in the front cover in order to achieve reductions in thickness and weight. In order to achieve weight reduction, Japanese Patent Laid-Open No. 2009-42350 has proposed an apparatus configured to join two exterior members with an electrically disbonding adhesive.

Figure 1:
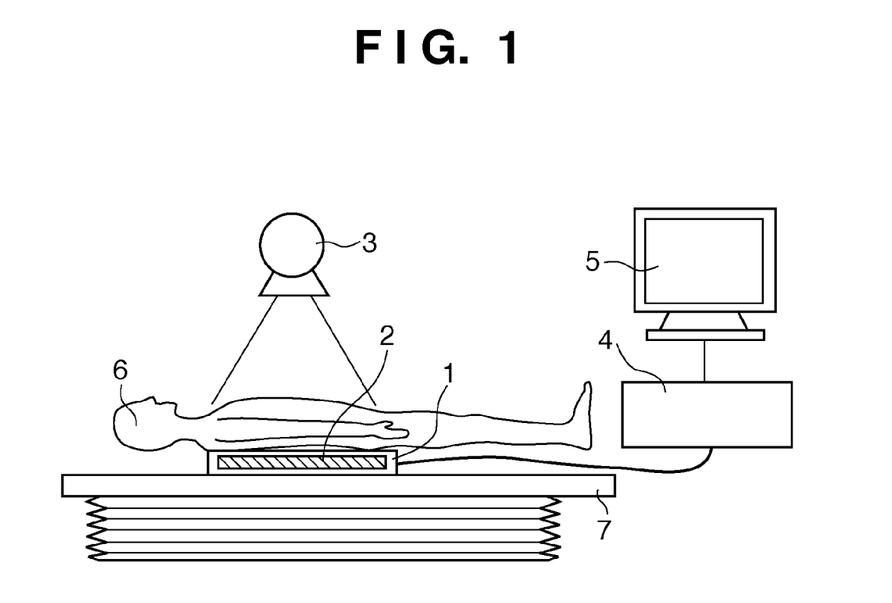
FIG. 1 is a view showing the arrangement of a general system using an X-ray imaging apparatus.

In general, improving the strength of an apparatus itself while protecting the interior of the apparatus will increase the weight and size of the apparatus itself. As shown in FIG. 1, a portable X-ray imaging apparatus is sometimes inserted under an object 6 to image it on a table in an X-ray room, on a bed in a hospital ward, or on an operating table in an operating room. For this reason, an X-ray imaging apparatus 1 is required to be thinner to reduce the discomfort experienced by a patient. When inserting the X-ray imaging apparatus 1 under the object 6 at the time of imaging, an X-ray technician who operates the X-ray imaging apparatus 1 needs to hold the apparatus with one hand. When using an X-ray imaging apparatus on a nursing cart on a side of a bed in a hospital ward, a technician needs to set the X-ray imaging apparatus while holding the posture of a patient by himself/herself. The apparatus is therefore required to be smaller and lighter for a reduction in load on the part of the technician as well.

In the X-ray imaging apparatus 1, the housing for protecting an X-ray sensor 2 accounts for most of the weight. The housing is roughly divided into two parts. In many cases, one part is placed on the X-ray incident side of the X-ray sensor 2, and the other part is placed on the opposite side to the X-ray incidence side of the X-ray sensor 2. A metal material such as an aluminum alloy or a magnesium alloy is often used for the housing on the X-ray incident side to achieve a reduction in weight. CFRP is often used for part in the X-ray incident range because of the necessity to have a high X-ray transmittance. With the recent downsizing of imaging apparatuses, an X-ray transmission member occupies most of the housing on the X-ray incident side. A metal material such as an aluminum alloy or a magnesium alloy is often used for the housing on the opposite side to the X-ray incident side to reduce the influence of external noise on the housed X-ray sensor 2 and reduce the weight.

When different kinds of materials are used for the housing in this manner, since they have different thermal expansion coefficients, a change in the temperature of the housing due to a change in ambient temperature will deform the housing of the imaging unit. When such an apparatus is transported by air or sea, changes in temperature are greater than those in normal usage. This increases the risk of deforming the housing of the imaging unit and imposing adverse effects on the housed X-ray sensor 2. Although it is possible to solve this problem by making a design for increasing the rigidity and suppressing deformation, for example, increasing the thickness of the housing, this contradicts the attempt to reduce the size and weight of the apparatus.

In the apparatus disclosed in Japanese Patent Laid-Open No. 2006-212175, holes are formed in the front cover on the X-ray incident side, and engagement pins are provided on the housing containing the X-ray sensor 2. The pins are fitted in the holes of the front cover to form the exterior of the housing. To prevent the removal of the front cover, the cover is sandwiched between sandwiching members. According to this structure, however, severe machining accuracy is required in terms of a plurality of pins existing along the outer periphery of the housing and the positions of holes of the front cover which engage with the pins, resulting in high component costs. In addition, the following problem is still unsolved. Since different materials are used for the front cover and the housing, and they engage with each other, great changes in ambient temperature at the time of, for example, the transportation of the apparatus will deform the apparatus due to the difference in thermal expansion coefficient between the front cover and the housing. This affects the X-ray sensor 2 inside the apparatus.

In the apparatus disclosed in Japanese Patent Laid-Open No. 2009-42350, although the X-ray sensor 2 is covered by the two exterior members, they are joined to each other with an electrically disbonding adhesive. In some cases, different materials are used for these two exterior members in consideration of X-ray transmission and strength securement. For this reason, as in the case of Japanese Patent Laid-Open No. 2006-212175, great changes in ambient temperature at the time of, for example, the transportation of the apparatus may deform the apparatus due to the difference in thermal expansion coefficient between the front cover and the housing. This may affect the X-ray sensor inside the apparatus. Furthermore, since the exterior members are joined to each other with a special adhesive, it is necessary to use dedicated equipment for separating the two exterior members when performing maintenance inside the apparatus. In addition, bonding the exterior members again after the maintenance will require a cumbersome process of removing the adhesive adhering to the members.

SUMMARY OF INVENTION

The present invention provides an X-ray imaging apparatus which is robust against changes in temperature and achieves reductions in weight and size by a housing connecting method while protecting an X-ray sensor inside the apparatus against external loads and shocks.

According to one aspect of the present invention, there is provided an X-ray imaging apparatus including an X-ray irradiation unit which irradiates X-rays, a detection unit which detects the X-rays transmitted through an object, and a housing which contains the detection unit, the housing comprising: a first housing in which an X-ray transmission member which transmits the X-rays is placed in an incident range of the X-rays irradiated from the X-ray irradiation unit; a second housing which supports the detection unit while being spaced apart from the X-ray transmission member on an opposite side to an incident side on which the X-rays strike the X-ray transmission member; and a plurality of connecting members which connect the first housing to the second housing, wherein the plurality of connecting members constrain relative movement between the first housing and the second housing in an irradiating direction of the X-rays irradiated from the X-ray irradiation unit, and the plurality of connecting members connect the first housing to the second housing so as to allow relative movement therebetween in a direction perpendicular to the irradiating direction of the X-rays.

The present invention can provide an X-ray imaging apparatus which is robust against changes in temperature and achieves reductions in weight and size by a housing connecting method while protecting an X-ray sensor inside the apparatus against external loads and shocks.

Further features of the present invention will become apparent from the following description of exemplary embodiments with reference to the attached drawings.

DESCRIPTION OF EMBODIMENTS (First Embodiment)

The arrangement of a general system using an X-ray imaging apparatus will be described with reference to FIG. 1. An X-ray imaging apparatus 1 incorporates an X-ray sensor 2. An X-ray generator 3 (X-ray irradiation unit) which irradiates X-rays is provided above the X-ray imaging apparatus 1. The X-ray generator 3 irradiates an object 6 with X-rays. The X-rays transmitted through the object 6 are converted into visible light through a phosphor. Photoelectric conversion elements arrayed in a two-dimensional lattice pattern detect the visible light as electrical signals. The X-ray imaging apparatus 1 includes a control unit which controls read driving, image transfer, and the like. An image processing unit 4 digitally processes an image output from the X-ray imaging apparatus 1. A monitor 5 then displays a radiographic image of the object 6. The X-ray imaging apparatus 1 includes a housing which contains the X-ray sensor 2.

The arrangement of the housing of the X-ray imaging apparatus according to the first embodiment will be described with reference to FIGS. 2A, 3, and 4. FIG. 3 is a view of the housing of the X-ray imaging apparatus shown in the perspective view of FIG. 2A when viewed from the X-ray irradiation side. This view is partially cut away to reveal the interior. FIG. 4 is a sectional view of a portion taken along the chain line (X-X) in FIG. 3.

Figure 2A:
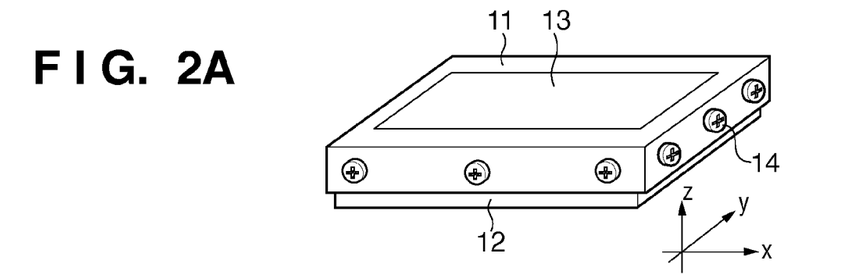
FIGS. 2A to 2E are perspective views for explaining the arrangement of the housing of the X-ray imaging apparatus.
Figure 3:
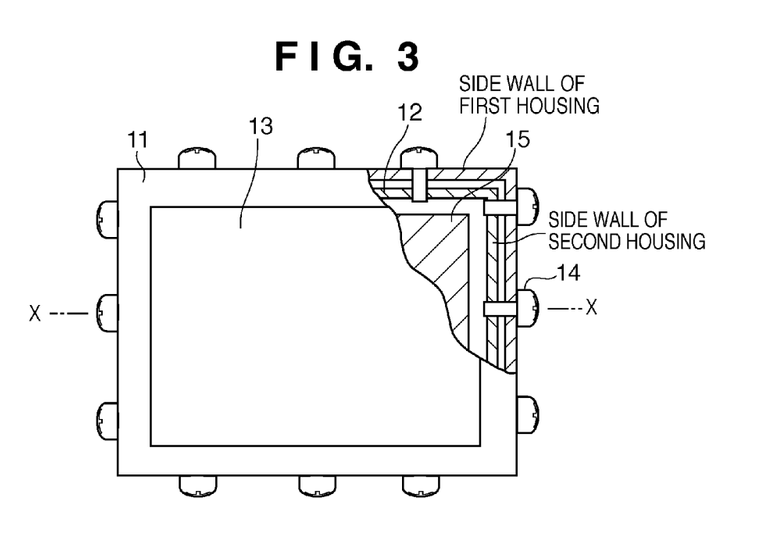
FIG. 3 is a view of the housing of the X-ray imaging apparatus shown in the perspective view of FIG. 2A when viewed from the X-ray irradiation side.
Figure 4:
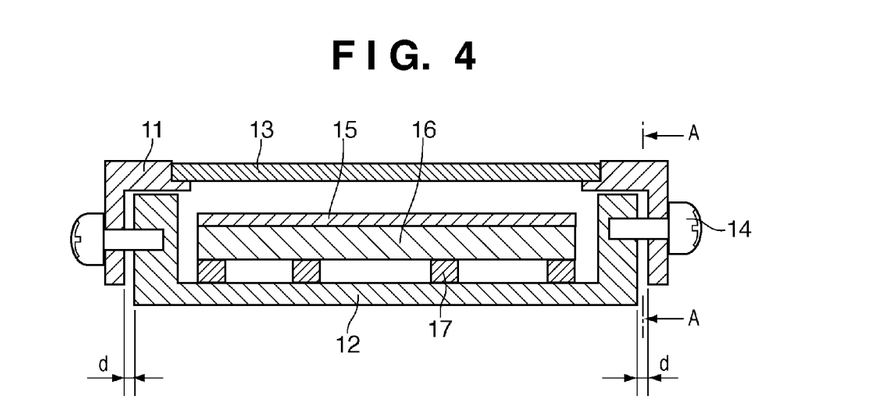
FIG. 4 is a sectional view of a portion taken along the chain line (X-X) in FIG. 3.

Referring to FIGS. 2A, 3, and 4, a first housing 11 is located on the X-ray incident side and formed from a lightweight, rigid metal material such as an aluminum alloy or a magnesium alloy. An X-ray sensor 15 is supported by a support base 16 and is fixed to a second housing 12 located on the opposite side to the X-ray incident side with a fastening portion 17. Like the first housing 11, the second housing 12 is also formed from a lightweight, rigid metal material such as an aluminum alloy or a magnesium alloy. An X-ray transmission member 13 which transmits X-rays is placed and joined on the first housing 11 in the incident range of irradiated X-rays. For example, CFRP which is a lightweight, rigid material can be used for the X-ray transmission member 13.

As shown in FIGS. 3 and 4, the side walls of the first housing 11 and the side walls of the second housing 12 are arranged outside the projection surface of the X-ray sensor, when viewed from the X-ray incident direction, such that the side walls of the housings overlap each other while being spaced apart from each other. At this overlapping portion, a gap d is provided between the first housing 11 and the second housing 12, and the housings are connected to each other with a plurality of connecting members (screws 14). The plurality of connecting members constrain the relative movement between the first housing 11 and the second housing 12 in the irradiating direction of irradiated X-rays. The plurality of connecting members 14 connect the first housing 11 and the second housing 12 so as to make them relatively move in a direction perpendicular to the irradiating direction of X-rays.

Figure 5:
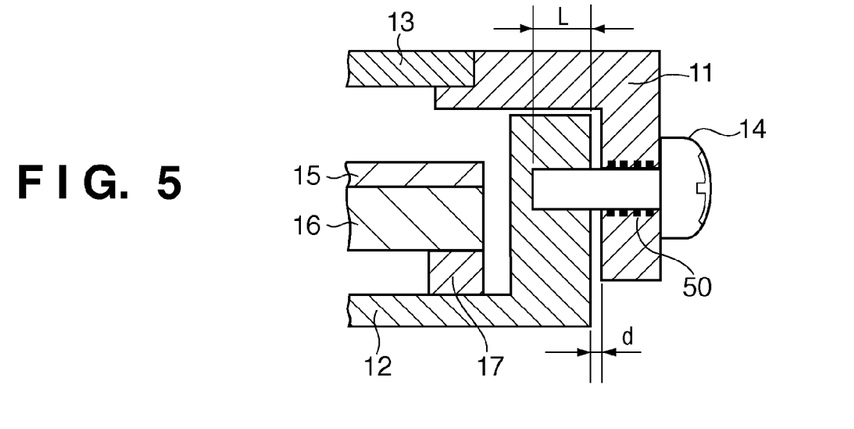
FIG. 5 is a view for explaining a screw connecting portion in FIG. 4.
Figure 6:
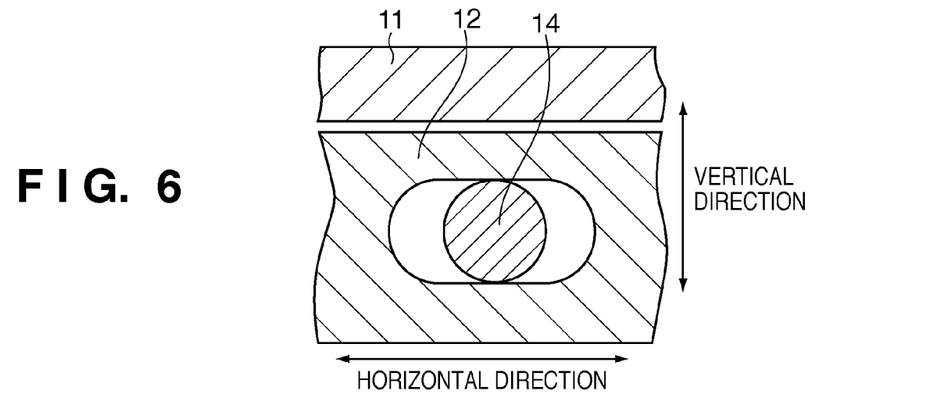
FIG. 6 is a view showing part of the A-A cross-section of FIG. 4.

The screw connecting portion in FIG. 4 will be described with reference to FIG. 5. Each of the plurality of connecting members 14 includes a screw portion which engages with a tap portion formed on the first housing 11 and a pin portion (a portion fitted in a concave portion may be a pin portion or a screw portion) fitted in a concave portion formed in the second housing 12. The screw 14 is fixed by a tap portion 50 provided on the first housing 11. The second housing 12 has a round hole long enough to receive the leg portion of the screw 14. The leg portion of the screw 14 is thus housed in this long round hole. FIG. 6 shows part of the A-A cross-section of FIG. 4. FIG. 6 shows a state in which the leg portion of the screw 14 is fitted in the long round hole provided in the second housing 12. This hole has a margin relative to the outer diameter of the screw 14 in the horizontal direction, and is fitted to the screw 14 without any backlash in the vertical direction. Referring to FIG. 5, L represents the engagement amount of the leg portion of the screw 14 by which it is fitted in the hole (concave portion) formed in the second housing. The use of a general-purpose screw as the screw 14 is advantageous in terms of cost. However, the portion corresponding to the engagement amount L of the screw 14 may be a parallel pin without any threaded portion. With this structure, the first housing 11 is connected to the second housing 12. The engagement amount L of the leg portion of the screw 14 has a value larger than a maximum value dmax of the gap d formed when the housing expands or contracts due to the influences of the offset between the first housing 11 and the second housing 12 and heat or when the housing deforms upon receiving external force such as a shock.

With this structure, the relative positional relationship between the first housing 11 and the second housing 12 is set such that the housings are connected to each other so as to have a slight degree of freedom in the x and y-directions in FIG. 2A, while the degree of freedom of movement is restricted in the z-axis direction.

In general, CFRP as an X-ray transmission member has a small thermal expansion coefficient and exhibits a small expansion/contraction amount with a change in temperature. A metal material has a larger thermal expansion coefficient than CFRP. When a temperature change occurs, the first housing 11 and the second housing 12, which hold the X-ray transmission member 13, expand/contract by different amounts due to different thermal expansion coefficients. Using the connecting method like this embodiment can absorb a difference in expansion/contraction amount and suppress the deformation of the overall X-ray imaging apparatus because the housing connecting portion has a degree of freedom in the x-y plane in FIG. 2A. Using such a connecting structure can suppress the deformation of the apparatus even if a material having a larger thermal expansion coefficient, for example, a resin, is used. The same effect can be obtained even if the second housing 12 is entirely made of an X-ray transmission member. In this manner, it is possible to provide an apparatus which can suppress the deformation of the apparatus, without increasing the rigidity by increasing the thickness of the apparatus housing, when a temperature change occurs, and achieve reductions in size and weight so as to cope with changes in temperature.

Figure 7:
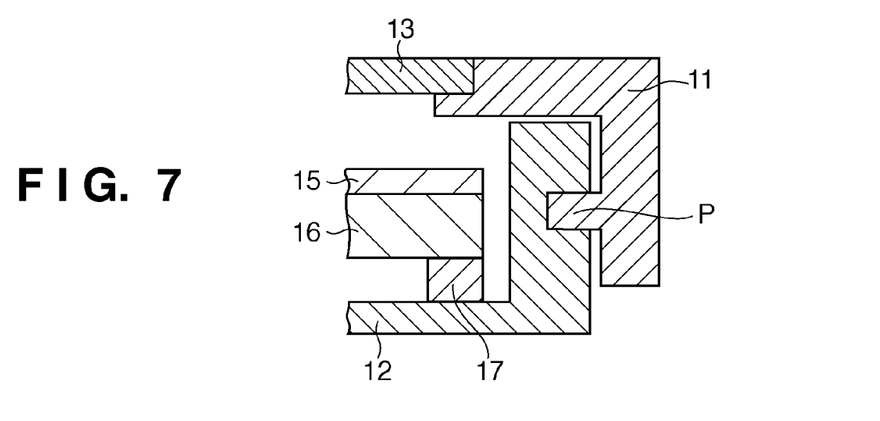
FIG. 7 is a view showing a modification of the connecting member.

In this embodiment, the connecting portions formed by the screws 14 which restrict movement are provided at three portions on one side wall. However, the gist of the present invention is not limited to this example. The number of portions at which the side walls are connected may be increased or decreased in accordance with the size of the housing or the need for them. In addition, the portions at which the side walls are connected to each other may be linear or planar portions as well as points. For example, as shown in FIG. 7, it is possible to provide projecting portions P for the first housing 11 as members for connection (connecting members), instead of the screws 14, and make the projecting portions P engage with the second housing 12 having the same structure as that shown in FIGS. 6 and 7.

This embodiment can provide an X-ray imaging apparatus which is robust against changes in temperature and achieves reductions in weight and size by the housing connecting method which solve the above problems while protecting the X-ray sensor inside the apparatus against external loads and shocks.

(Second Embodiment)

FIGS. 2A and 4 show an example of the overlapping relationship between the side walls provided for a first housing 11 and second housing 12 which incorporate an X-ray sensor 15. That is, the first housing 11 is located outside the second housing 12. This relationship eliminates the chance that a liquid adhering, by any possibility, to the X-ray incident side will enter a gap portion d provided between the first housing 11 and the second housing 12. This makes it possible to always maintain the apparatus clean. Stacking the first housing 11 on the second housing 12 can not only shield the interior of the housing against light but also increase the strength of the X-ray imaging apparatus when its side surface receives a shock because the side wall has a double structure.

Figure 2B:
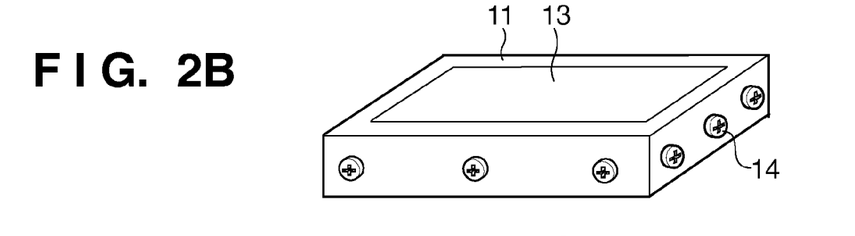
Figure 8:
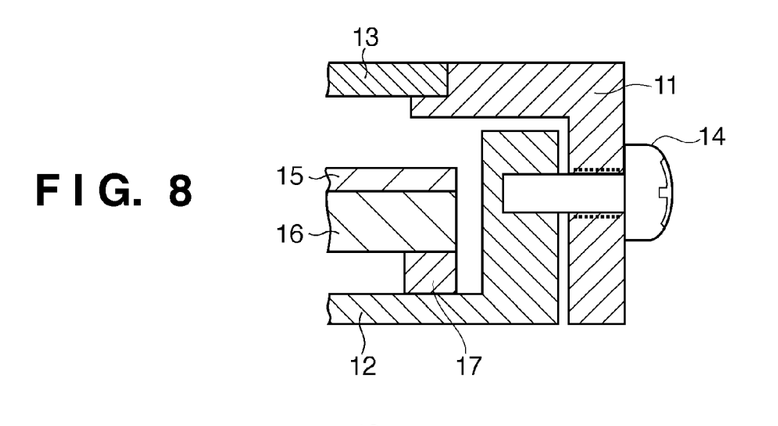
FIG. 8 is a view showing a cross-section of the housing of the X-ray imaging apparatus shown in the perspective view of FIG. 2B.

FIG. 2B is a view showing the first modification of the overlapping relationship between the side walls provided for the first housing 11 and second housing 12 as the arrangement of the second embodiment. FIG. 8 shows a cross-section of FIG. 2B. The side walls of the first housing 11 are formed to entirely cover the outer peripheries of the side walls of the second housing 12. This structure eliminates the difference in level between the side walls of the first housing 11 and the side walls of the second housing 12, and attains an integral design. As shown in FIG. 2B, in the arrangement obtained by assembling the first housing 11 and the second housing 12, since the second housing 12 is not a portion which is directly and visually perceived as the exterior of the apparatus, it is possible to omit the process of finishing the exterior of the second housing 12 to improve its appearance. This can reduce the manufacturing cost.

Figure 2C:
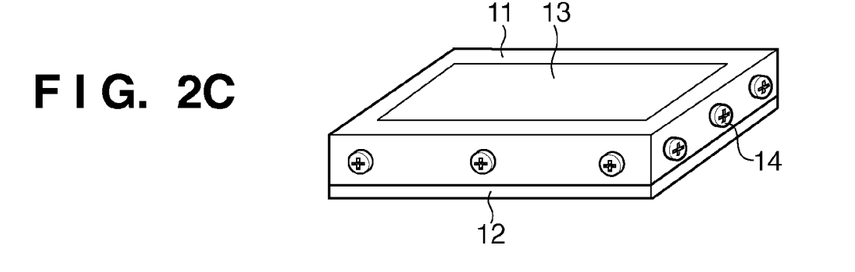
Figure 9:
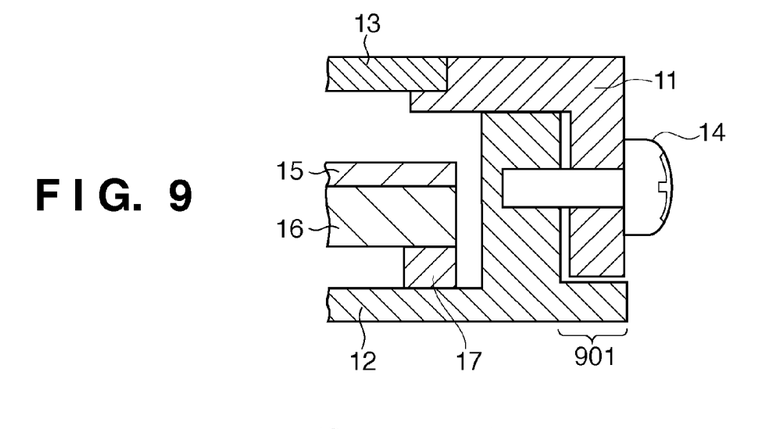
FIG. 9 is a view showing a cross-section of the housing of the X-ray imaging apparatus shown in the perspective view of FIG. 2C.

FIG. 2C shows the second modification of the overlapping relationship between the side walls provided for the first housing 11 and second housing 12. FIG. 9 shows a cross-section of FIG. 2C. The second housing 12 has a convex cross-sectional shape. The side walls of the first housing 11 fall within protruding regions 901 of the bottom surface portion of the second housing 12. This eliminates the difference in level between the side walls of the first housing 11 and those of the second housing 12. Using this structure can also eliminate the difference in level between the side walls of the apparatus, and provides a superior effect in mounting a side surface cover 21 (to be described later).

Figure 2D:
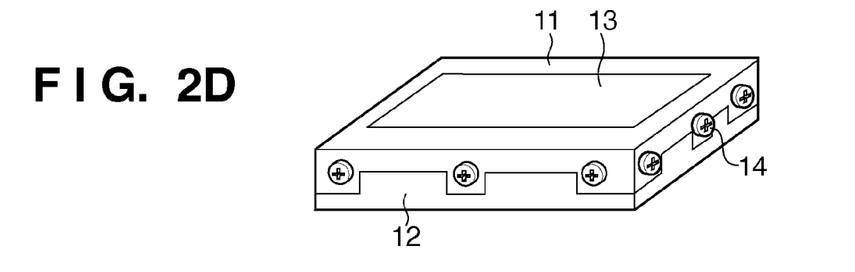
Figure 2E:
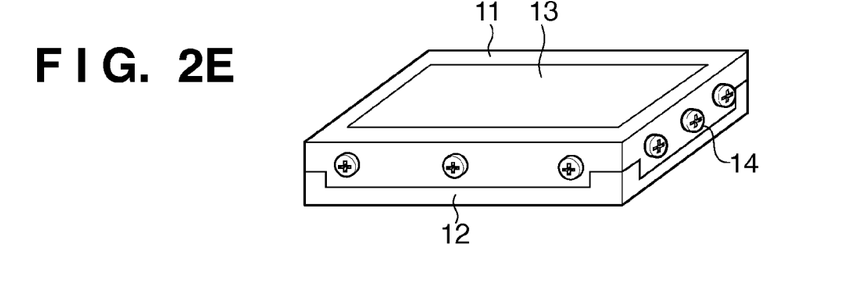

FIGS. 2D and 2E each show an example of changing the dividing line of the housing which can disperse the shock which the housing receives. When the X-ray imaging apparatus receives a shock due to a drop or the like, the first housing 11 and the second housing 12 receive the shock. The housing structure of the present invention is made small and light. For this reason, when a side surface or corner portion of the apparatus receives a shock, the shock is dispersed to both the first housing 11 and the second housing 12. Changing the dividing line of the housing can optimize the shapes of the first housing 11 and second housing 12 and secure the strength enough to protect the X-ray sensor 15 inside the apparatus even if a side surface or a corner portion receives a shock.

Figure 10:
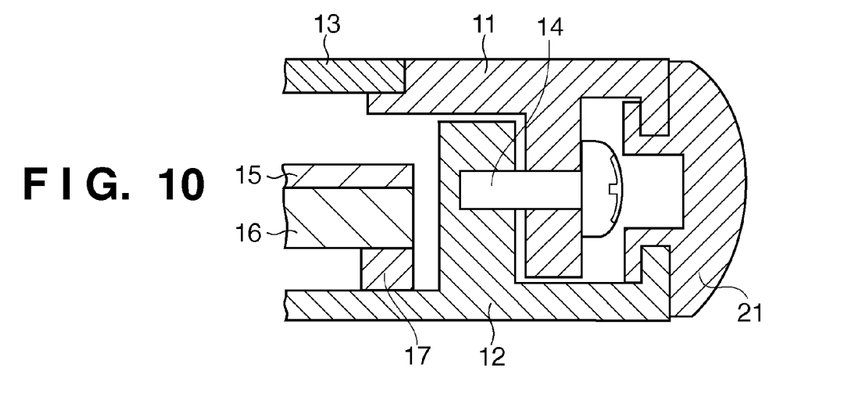
FIG. 10 is a view showing a structure configured to mount a side surface cover on the first and second housings.

In these examples, screws 14 on the side walls protrude relative to the first housing 11. It is possible to avoid the protrusion of the screws 14 from the first housing 11 by providing countersunk holes (concave portions) for portions of the first housing 11 at which the screws 14 are fixed. As shown in FIG. 10, it is also possible to conceal the screws by providing the first housing 11 and the second housing 12 with a structure for mounting the side surface cover 21 and mounting the cover. This makes it possible to conceal the dividing portion between the housings with the cover. This can reduce the shock acting on a side surface or a corner portion and improve the appearance.

This embodiment can provide an X-ray imaging apparatus which is robust against changes in temperature and achieves reductions in weight and size by the housing connecting method which solve the above problems while protecting the X-ray sensor inside the apparatus against external loads and shocks.

(Third Embodiment)

Figure 11:
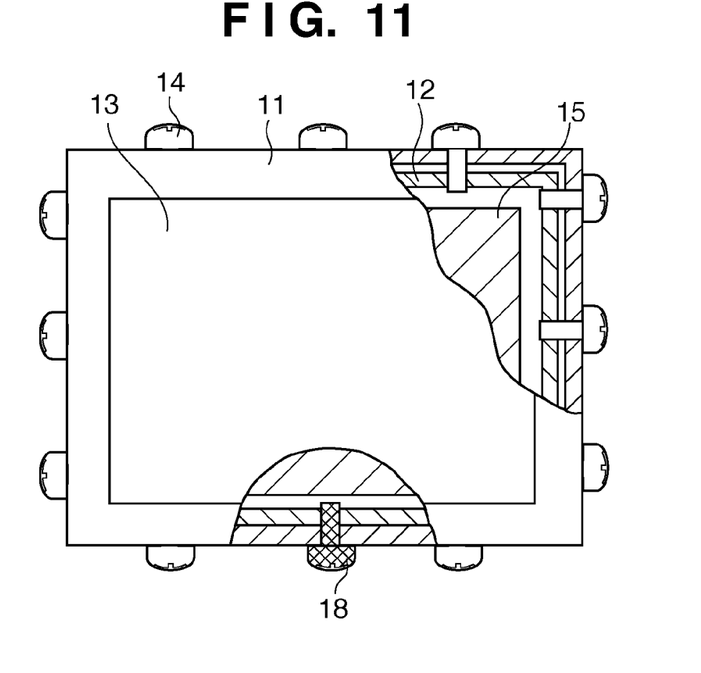
FIG. 11 is a view for explaining an example of the arrangement of the housing of an X-ray imaging apparatus according to the third embodiment.
Figure 12:
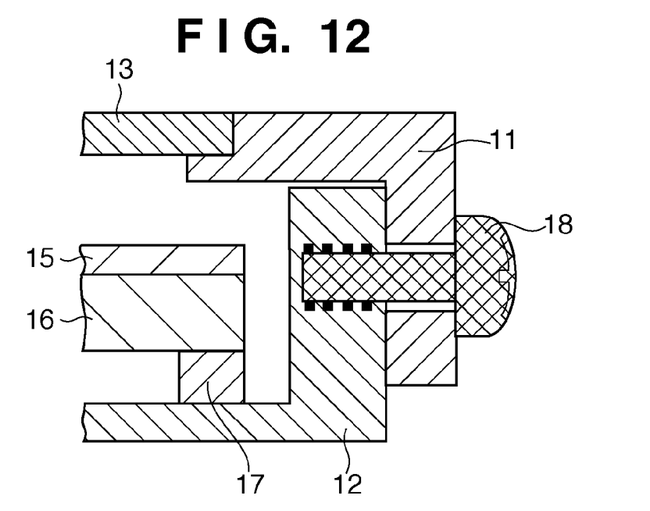
FIG. 12 is a view exemplifying the arrangement of a connecting member in the third embodiment.

The third embodiment of the present invention will be described with reference to FIG. 11. One screw 18 on one of the side walls of a first housing 11 and second housing 12, which functions as a constraint connecting member restricts the movement of the first housing 11 and second housing 12 in the X-, Y-, and Z-axis directions (all directions). FIG. 12 is a cross-sectional view showing a portion at which the screw 18 is fixed. The screw 18 engages with a tap provided for the second housing 12 to be fastened. Fastening the screw 18 will fix the first housing 11 and the second housing 12. The side walls of the first housing 11 are then in contact with those of the second housing 12.

Figure 13A:
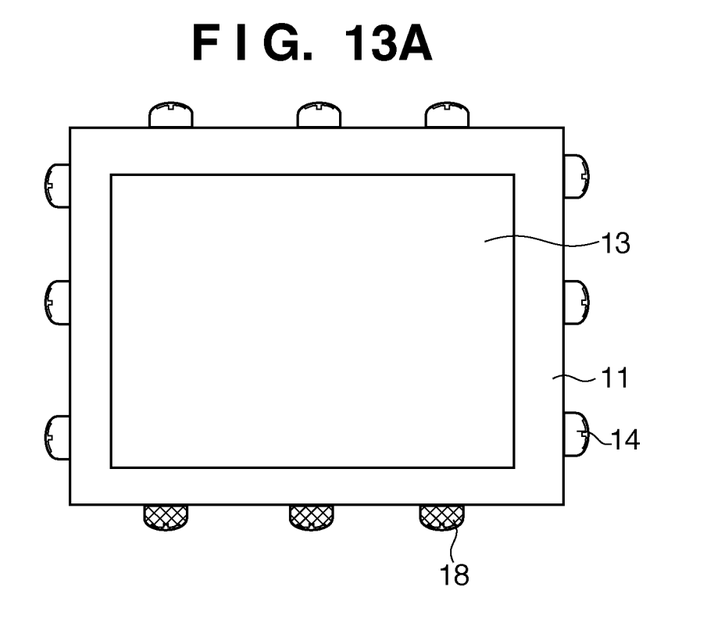
FIGS. 13A and 13B are views exemplifying the arrangement of the connecting member in the third embodiment.
Figure 13B:
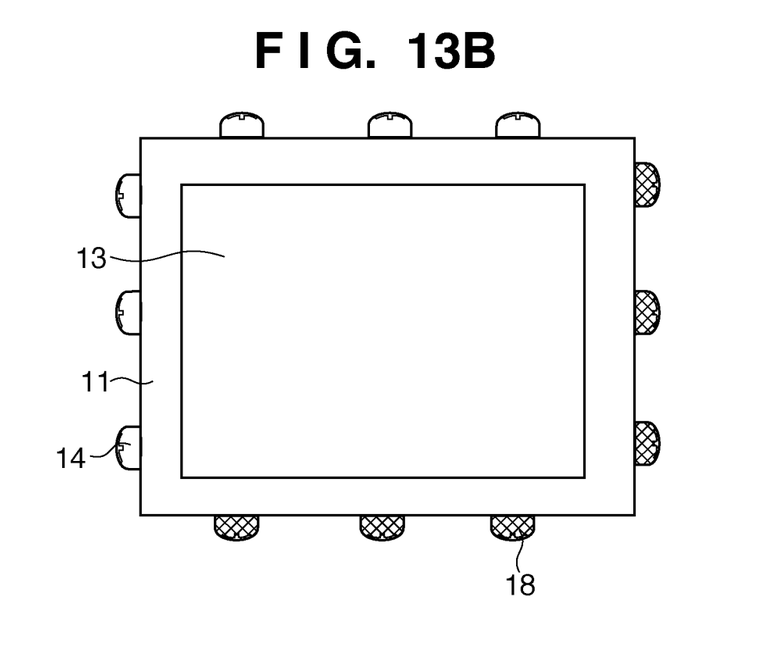

Remaining screws 14 restrict only the movement of the housings in the X-ray incident direction (the movement in the Z-axis direction) by using the same connecting method as that in the first embodiment. The housings are made to have degrees of freedom in the remaining directions (movement in the X- and Y-axis directions). FIG. 13A shows an example in which three screws 18 (constraint connecting members) on one side wall restrict the movement of the first housing 11 and second housing 12 in the X-, Y-, and Z-axis directions (all directions). FIG. 13B shows an example in which three screws 18 on each of two side walls restrict the movement of the first housing 11 and second housing 12 in the X-, Y-, and Z-axis directions (all directions). This structure uniquely determines the relative positional relationship between the first housing 11 and the second housing 12. In addition, integrating the first housing 11 and the second housing 12 makes it possible to expect an increase in strength.

In this manner, even when the first housing 11 is connected to the second housing 12 at several portions by fastening or the like, ensuring the direction in which stress is released can suppress the deformation of the apparatus even if the housings expand/contract due to changes in temperature.

Figure 14A:
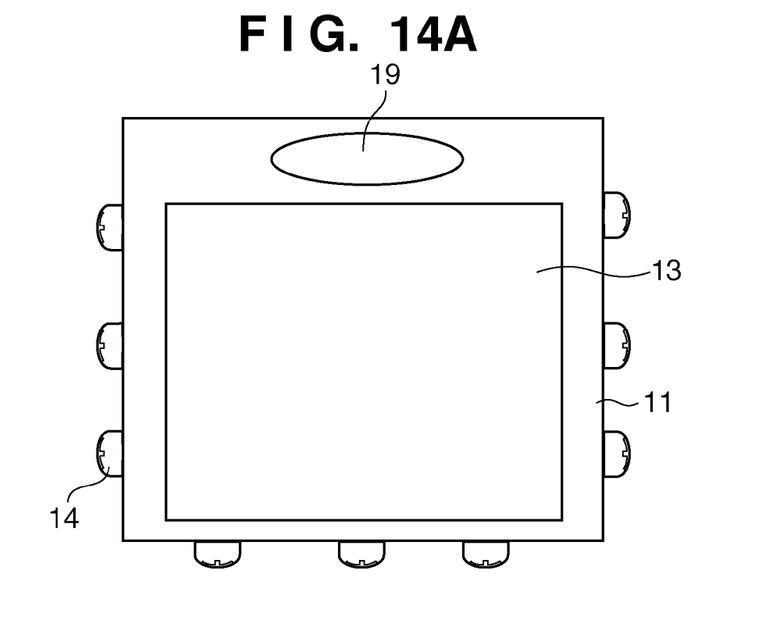
FIGS. 14A and 14B are views exemplifying the arrangement of the housing of the X-ray imaging apparatus according to the third embodiment.
Figure 14B:
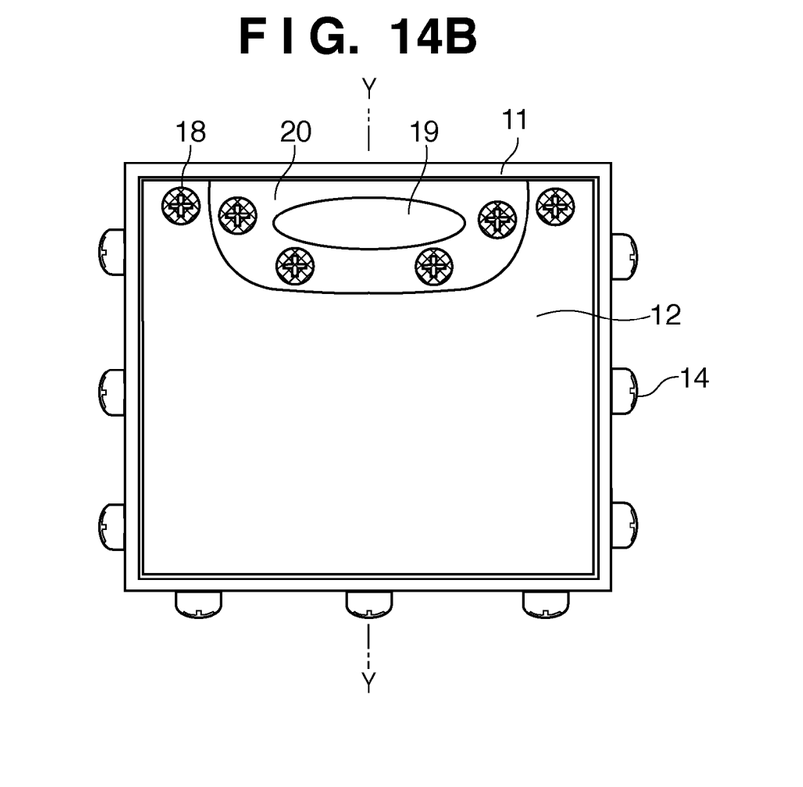
Figure 15A:
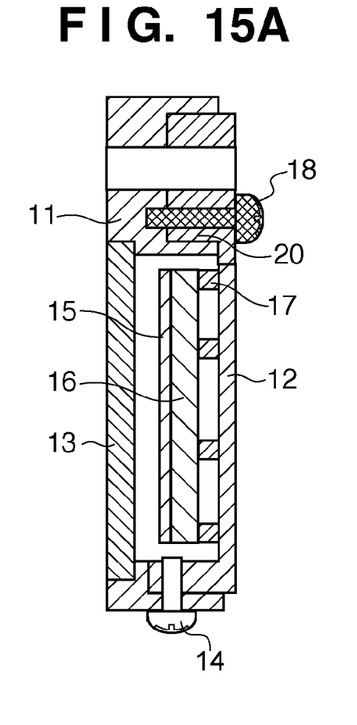
FIGS. 15A and 15B are views for explaining the arrangement of the housing of the X-ray imaging apparatus according to the third embodiment.
Figure 15B:
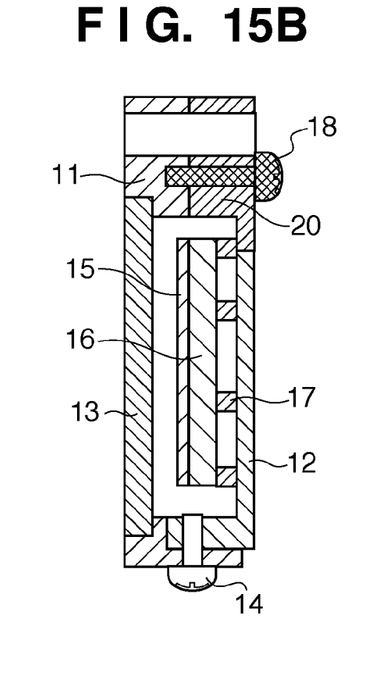

FIGS. 14A, 14B, and 15A each show an example in which the X-ray imaging apparatus is provided with a handle 19 for carrying the apparatus and a maintenance cover 20 on the second housing 12 side. FIG. 14A is a view of the apparatus when viewed from the X-ray incident direction. FIG. 14B is a view of the apparatus when viewed from a direction opposite to the X-ray incident direction. FIG. 15A is a sectional view taken along Y-Y of FIG. 14B. When the apparatus includes the maintenance cover 20 and the handle 19, as shown in FIG. 14B, the housings are fastened with screws from the side opposite to the X-ray incident direction, and fixing with screws 18 at this portion restricts the movement of the housings in all the directions. The housings may be divided as shown in FIG. 15B at the side wall on the handle 19 side. This allows the maintenance cover 20 to have a large opening portion, and hence facilitates operation at the time of maintenance. In this case, the first housing 11 and the second housing 12 do not have a double wall structure in which their side walls overlap each other while being spaced apart from each other by a gap d. However, in consideration of the time when, for example, the user carries the apparatus while holding the handle 19, this structure prevents the handle 19 side from facing downward when the apparatus is dropped. This therefore prevents the handle 19 side from directly receiving a shock.

When the apparatus includes a handle and a maintenance cover as described above, ensuring the direction in which stress is released can suppress the deformation of the apparatus even when the housings expand/contract due to changes in temperature.

(Fourth Embodiment)

Figure 16:
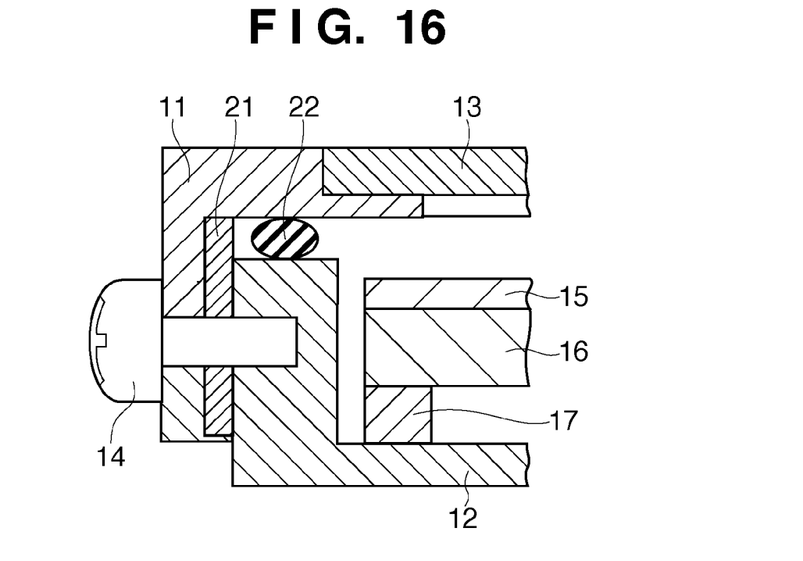
FIG. 16 is a view for explaining an example of the arrangement of the housing of an X-ray imaging apparatus according to the fourth embodiment.

The arrangement of the housing of an X-ray imaging apparatus according to the fourth embodiment will be described with reference to FIG. 16. FIG. 16 shows the cross-sectional shape of the overlapping portion between a side wall of a first housing 11 and a side wall of a second housing 12. An elastic member 21 and an elastic member 22 are inserted in the space (gap portion) provided between the first housing 11 and the second housing 12. The elastic member 21 prevents the side walls of the first housing 11 from coming into contact with the side walls of the second housing 12 in the horizontal direction. The elastic member 22 prevents the first housing 11 from coming into contact with the second housing 12 in the vertical direction. Inserting the elastic member 21 between the side walls of the first housing 11 and the side walls of the second housing 12 can suppress the generation of noise when vibration occurs and the housings come into contact with each other. In addition, the elastic member 21 reduces the shock acting on the apparatus when it is dropped, and hence reduces the shock acting on a housed X-ray sensor 15. In addition, depending on the material selected, it is possible to prevent a liquid from entering from the outside of the apparatus into the housing.

Inserting the elastic member 22 makes it possible to have the same effect as that obtained by inserting the elastic member 21. In addition, when an object is placed on the X-ray incident side of the X-ray imaging apparatus, and the apparatus receives a load, the elastic member 22 can receive part of the load. This can reduce the load acting on screws 14.

This embodiment can provide an X-ray imaging apparatus which is robust against changes in temperature and achieves reductions in weight and size by the housing connecting method which solve the above problems while protecting the X-ray sensor inside the apparatus against external loads and shocks.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-137724, filed Jun. 8, 2009, which is hereby incorporated by reference herein in its entirety.

The invention claimed is:

1. An X-ray imaging apparatus comprising:
a detection unit which detects X-rays; and
a housing which contains said detection unit,
wherein said housing includes:
   a first housing having a portion extending along a first direction and a portion extending along a second direction perpendicular to the first direction, which surround an X-ray transmission member which transmits the X-rays, and first side walls provided along a third direction perpendicular to the first and second directions;
   a second housing which has second side walls provided along the third direction and arranged opposite to said first housing so that said detection unit is sandwiched between said first housing and said second housing; and
   a plurality of connecting members which connect said first housing to said second housing, wherein said plurality of connecting members fix relative position between said first housing and said second housing in the third direction, and said plurality of connecting members connect said first side walls to said second side walls so as to allow relative movement in at least one direction of the first direction and the second direction.

2. The apparatus according to claim 1, wherein said plurality of connecting members each comprise a screw portion and a pin portion, and said first side walls have a tap portion, and said second side walls have a concave portion formed therein, and wherein said screw portions each engage with said tap portion formed on said first side walls, and said pin portions each are fitted in said concave portion formed in said second side walls.

3. The apparatus according to claim 1, wherein said plurality of connecting members comprise at least one constraint connecting member which constrains relative movement between said first housing and said second housing in the first direction and the second direction.

4. The apparatus according to claim 3, wherein said constraint connecting member comprises a pin portion, and said first side walls have a concave portion formed therein, and said second side walls have a tap portion formed thereon, and wherein said pin portion is fitted in said concave portion formed in said first side walls and said screw portion engages with said tap portion formed on said second side walls.

5. The apparatus according to claim 1, wherein said plurality of connecting members connect said first side walls to said second side walls and said first side walls are spaced apart from said second side walls.

6. The apparatus according to claim 5, further comprising an elastic member for preventing the first side walls from coming into contact with the second side walls, said elastic member being provided between the first side walls and the second side walls.

7. The apparatus according to claim 1, further comprising:
a first elastic member arranged in a space formed in a horizontal direction perpendicular to an irradiating direction of the X-rays between said first housing and said second housing; and
a second elastic member arranged in a space formed in the irradiating direction of the X-rays between said first housing and said second housing.

* * * * *